United States Patent [19]

Sugimori et al.

[11] Patent Number: 4,502,974
[45] Date of Patent: Mar. 5, 1985

[54] HIGH TEMPERATURE LIQUID-CRYSTALLINE ESTER COMPOUNDS

[75] Inventors: Shigeru Sugimori; Tetsuhiko Kojima, both of Kanagawaken, Japan

[73] Assignee: Chisso Corporation, Osaka, Japan

[21] Appl. No.: 477,973

[22] Filed: Mar. 23, 1983

[30] Foreign Application Priority Data

| Date | Country | Number |
|---|---|---|
| Mar. 31, 1982 | [JP] Japan | 57-53366 |
| May 20, 1982 | [JP] Japan | 57-85269 |
| May 20, 1982 | [JP] Japan | 57-85271 |
| May 31, 1982 | [JP] Japan | 57-92772 |
| Jun. 17, 1982 | [JP] Japan | 57-104365 |
| Jun. 23, 1982 | [JP] Japan | 57-107724 |
| Jul. 6, 1982 | [JP] Japan | 57-117409 |
| Jul. 21, 1982 | [JP] Japan | 57-127291 |
| Jul. 21, 1982 | [JP] Japan | 57-127295 |
| Aug. 2, 1982 | [JP] Japan | 57-134964 |
| Aug. 5, 1982 | [JP] Japan | 57-136658 |
| Aug. 11, 1982 | [JP] Japan | 57-139451 |
| Aug. 11, 1982 | [JP] Japan | 57-139452 |
| Aug. 24, 1982 | [JP] Japan | 57-146594 |
| Aug. 24, 1982 | [JP] Japan | 57-146595 |
| Aug. 30, 1982 | [JP] Japan | 57-150424 |
| Sep. 3, 1982 | [JP] Japan | 57-153601 |
| Oct. 5, 1982 | [JP] Japan | 57-175145 |
| Oct. 26, 1982 | [JP] Japan | 57-188047 |
| Nov. 4, 1982 | [JP] Japan | 57-193637 |
| Jan. 12, 1983 | [JP] Japan | 58-3254 |
| Jan. 27, 1983 | [JP] Japan | 58-11906 |

[51] Int. Cl.$^3$ ............ C09K 3/34; C07C 69/773; C07C 69/753; C07C 121/52; C07C 120/04; C07C 69/76

[52] U.S. Cl. .................. 252/299.63; 252/299.5; 350/350 R; 260/465 D; 560/102; 560/107; 560/108; 560/116

[58] Field of Search ............ 252/299.63, 299.5; 350/350 R; 560/72, 73, 65, 102, 107, 108, 116; 260/465 D

[56] References Cited

U.S. PATENT DOCUMENTS

| | | | |
|---|---|---|---|
| 4,229,315 | 10/1980 | Krause et al. | 252/299.63 |
| 4,261,652 | 4/1981 | Grat et al. | 252/299.63 |
| 4,340,498 | 7/1982 | Sugimori | 252/299.5 |
| 4,387,038 | 6/1983 | Fukui et al. | 252/299.63 |
| 4,387,039 | 6/1983 | Sugimori et al. | 252/299.63 |
| 4,399,298 | 8/1983 | Sugimori et al. | 252/299.5 |
| 4,400,293 | 8/1983 | Romer et al. | 252/299.63 |
| 4,405,488 | 9/1983 | Sugimori et al. | 252/299.63 |
| 4,410,445 | 10/1983 | Baur et al. | 252/299.63 |
| 4,415,470 | 11/1983 | Eidenschink et al. | 252/299.63 |

FOREIGN PATENT DOCUMENTS

| | | | |
|---|---|---|---|
| 19665 | 12/1980 | European Pat. Off. | 252/299.63 |
| 3211601 | 10/1983 | Fed. Rep. of Germany | 252/299.63 |
| 3231707 | 3/1984 | Fed. Rep. of Germany | 252/299.63 |
| 3335550 | 4/1984 | Fed. Rep. of Germany | 252/299.63 |
| 57-9742 | 1/1982 | Japan | 252/299.63 |
| 57-64645 | 4/1982 | Japan | 252/299.63 |
| 57-91953 | 6/1982 | Japan | 252/299.63 |
| 57-154158 | 9/1982 | Japan | 252/299.63 |
| 57-159743 | 10/1982 | Japan | 252/299.63 |
| 57-206647 | 12/1982 | Japan | 252/299.63 |
| 58-13542 | 1/1983 | Japan | 252/299.63 |
| 58-13544 | 1/1983 | Japan | 252/299.63 |
| 5375181 | 7/1983 | Japan | 252/299.65 |
| 58-126839 | 7/1983 | Japan | 252/299.63 |
| 58-118543 | 7/1983 | Japan | 252/299.63 |
| 58-121247 | 7/1983 | Japan | 252/299.63 |

OTHER PUBLICATIONS

Osman, M. A. et al., Mol. Cryst. Liq. Cryst., vol. 82 (Letters), pp. 331-338 (1983).

Primary Examiner—Teddy S. Gron
Attorney, Agent, or Firm—Fred Philpitt

[57] ABSTRACT

New liquid-crystalline ester compounds which exhibit a liquid-crystalline phase within a broad temperature range and have a positive, dielectric anisotropy, and a liquid-crystalline composition comprising the same are provided which ester compounds are expressed by the general formula

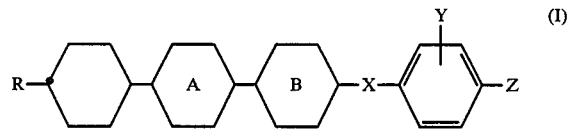

(I)

wherein R represents hydrogen atom or an alkyl group of 1 to 10 carbon atoms;

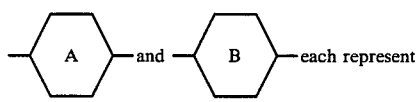

each represent

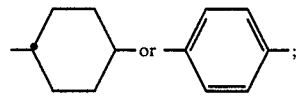

;

X represents

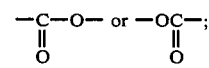

;

Y represents hydrogen atom, F, Cl or CN; and Z represents F, Cl or CN.

16 Claims, No Drawings

HIGH TEMPERATURE LIQUID-CRYSTALLINE ESTER COMPOUNDS

BACKGROUND OF THE INVENTION

1. Field of the Invention

This invention relates to novel liquid-crystalline substances exhibiting a liquid-crystalline phase within a broad temperature range and also having a positive dielectric anisotropy, and liquid-crystalline compositions containing the same.

2. Description of the Prior Art

Display elements using liquid crystals have come to be broadly used for watches, desk calculators, etc. Such liquid-crystalline display elements utilize properties of the optical anisotropy and dielectric anisotropy of liquid-crystalline substances, and the liquid-crystalline phase includes nematic liquid-crystalline phase, smectic liquid-crystalline phase and cholesteric liquid-crystalline phase. However, display elements utilizing nematic liquid crystals among the above-mentioned phases have been practically used most broadly. Further the display mode of such display elements include TN type (twisted nematic type), DS type (dynamic scattering type), guest-host type, DAP type, etc. and properties required for the liquid-crystalline substances used for the respective types are different. At any rate, however, it is preferred that the liquid-crystalline substances used for these display elements exhibit a liquid-crystalline phase within as broad a temperature range as possible in the natural world. At present, however, no single compound which satisfies by itself such conditions is present, and it is the present status that substances which are endurable to practical use for the present have been obtained by blending several kinds of liquid-crystalline compounds or non-liquid-crystalline compounds. Further, these substances should, of course, be stable to moisture, light, heat, air, etc. and also it is preferred for them that the threshold voltage and saturation voltage required for driving such display elements be as low as possible and their viscosities be as low as possible in order to make the response speed higher.

As compounds for satisfying such requirements, such compounds as expressed by the formulas

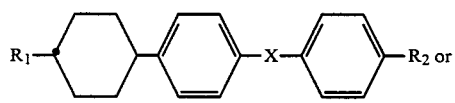

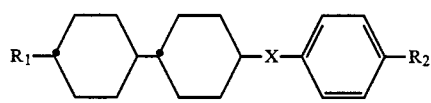

(wherein $R_1$ represents an alkyl group; X represents

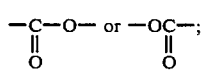

and $R_2$ represents an alkyl group, an alkoxy group or CN) disclosed in U.S. Pat. No. 4,229,315 have been well known and practically used. However, requirements for liquid-crystalline display elements have become severer, and in order to satisfy the requirements, liquid-crystalline compositions which exhibit a liquid-crystalline phase over the range from a lower temperature to a higher temperature have become necessary.

Now, in order to broaden the liquid-crystalline temperature range toward higher temperatures, it is necessary to use liquid-crystalline substances having a higher melting point as a component, but such liquid-crystalline substances having a higher melting point generally have a higher viscosity and hence liquid-crystalline compositions containing these also have a higher viscosity; thus the response speed, particularly that at lower temperatures, of liquid-crystalline display elements which are usable up to higher temperatures such as 80° C. have been liable to be notably retarded. The present inventors have made strenuous studies for obtaining liquid-crystalline substances satisfying the above-mentioned requirements, and have found liquid-crystalline substances which exhibit a liquid-crystalline phase up to higher temperatures and nevertheless have a lower viscosity.

SUMMARY OF THE INVENTION

The present invention resides in:
liquid crystalline ester compounds expressed by the general formula

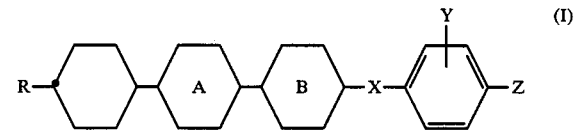

wherein R represents hydrogen atom or an alkyl group of 1 to 10 carbon atoms;

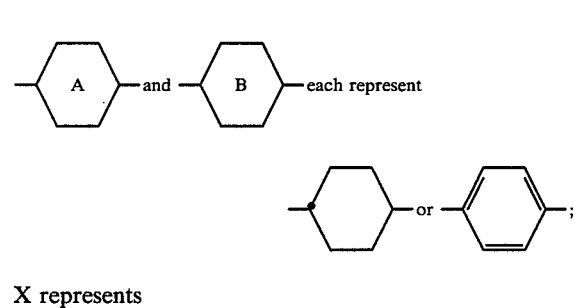

X represents

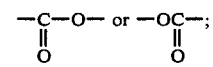

Y represents hydrogen atom, F, Cl or CN; and Z represents F, Cl or CN; and liquid-crystalline compositions containing at least one member of said ester compounds.

DESCRIPTION OF THE PREFERRED EMBODIMENTS

The compounds of the present invention exhibit a dielectric anisotropy value ($\Delta\epsilon$) which is as small as about +0.5 to 10; they also exhibit a liquid-crystalline phase up to higher temperatures; they can elevate the N-I point of liquid-crystalline compositions by being added in a small amount to the compositions; further particularly in the case of their halogen-substitutes, the values of threshold and saturation voltages are unchanged or not increased so much in spite of their $\Delta\epsilon$ values being reduced down to small values and also their viscosities are not elevated so much. Thus they are very useful compounds. Further they have superior stability to moisture, heat, light, air, etc.

The compounds of the formula (I) are concretely classified into these expressed by the following 17 formulas (II)~(XVIII) (wherein each R has the same definition as in the formula (I)):

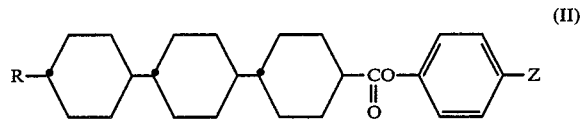
(II)

(wherein Z represents F, Cl or CN; this applies to the following formulas (III) and (IV))

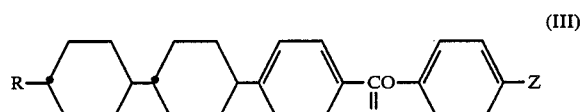
(III)

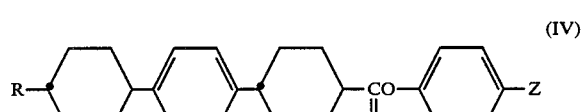
(IV)

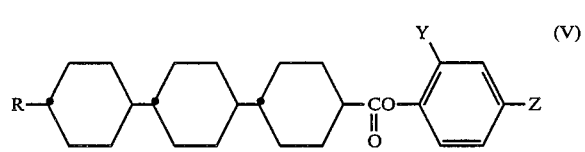
(V)

(wherein Y and Z each represent F or Cl; this applies to the following formulas (VI)~(XII))

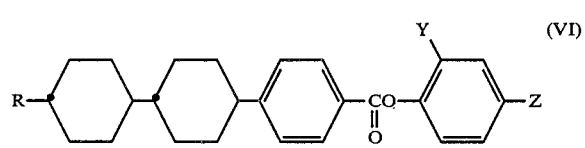
(VI)

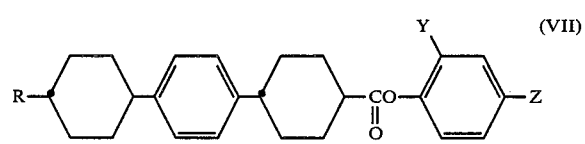
(VII)

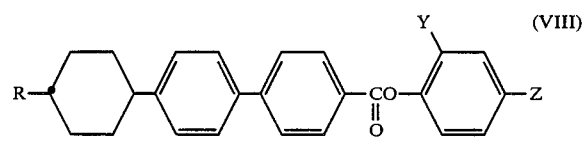
(VIII)

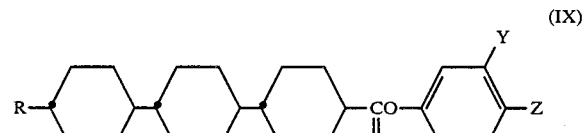
(IX)

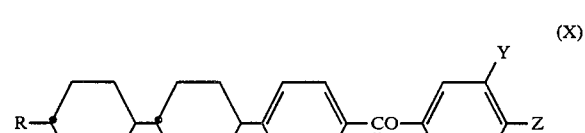
(X)

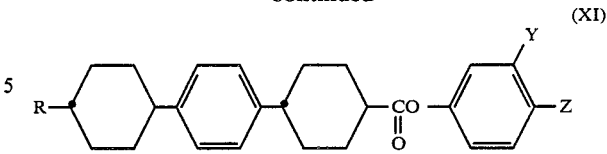
(XI)

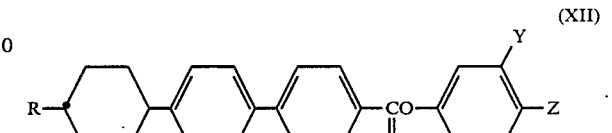
(XII)

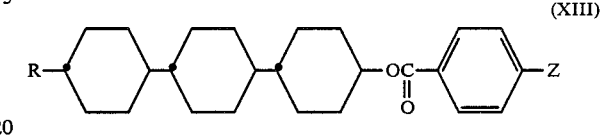
(XIII)

(wherein Z represents F, Cl or CN; this applies to the following formula (XIV))

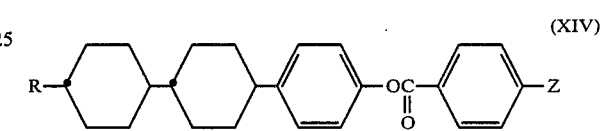
(XIV)

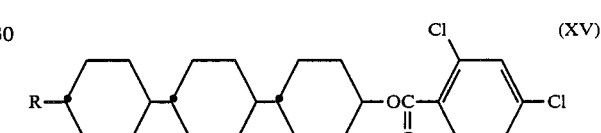
(XV)

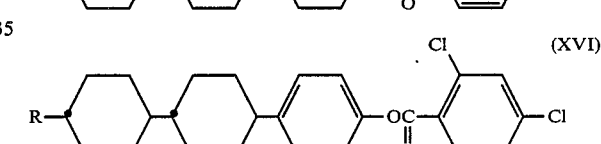
(XVI)

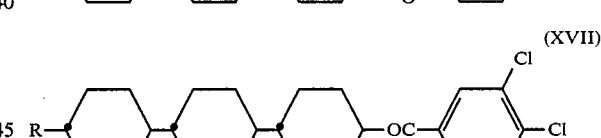
(XVII)

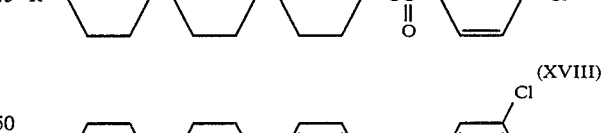
(XVIII)

Next, the methods for preparing the compounds of the present invention will be described.

Preparations of 4-[trans-4(trans-4-alkylcyclohexyl)-cyclohexyl]benzoic acids and trans-4″-alkyl-trans-octadecahydro-p-terphenyl-trans-4-carboxylic acids From bromobenzene and metallic Mg is prepared phenylmagnesium bromide, which is then reacted with a 4-(trans-4-alkylcyclohexyl)cyclohexanone to obtain a 4-(trans-4-alkylcyclohexyl)cyclohexan-1-ol-benzene, which is then dehydrated in the presence of potassium hydrogen sulfate as a catalyst to obtain a 4-(trans-4-alkylcyclohexyl)cyclohexen-1-yl-benzene, which is then hydrogenated in the presence of Raney Ni as a catalyst to obtain a trans-4-(trans-4-alkylcyclohexyl)-cyclohexylbenzene. This material may also be obtained directly by hydrogenation in the presence of Raney Ni. The material is then halogenated with iodic acid, periodic acid or the like to obtain a 4-[trans-4-(trans-4-alkylcyclohexyl)cyclohexyl]halogenobenzene, which is then cyanogenated with cuprous cyanide to obtain a 4-[trans-4-(trans-4-alkylcyclohexyl)cyclohexyl]benzonitrile, which is then hydrolyzed in a KOH aqueous solution-diethylene glycol system to prepare a 4-[trans-4-(trans-4-alkylcyclohexyl)cyclohexyl]benzoic acid (XIX). This benzoic acid derivative is reduced with metallic sodium in isoamyl alcohol to obtain a trans-4-alkyl-trans-octadecahydro-p-terphenyl-trans-4-carboxylic acid (XX). The above preparation is illustrated by the following chemical equations:

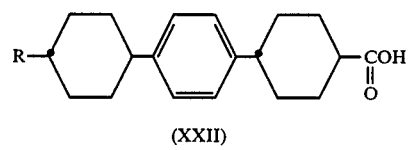

(XXII)

Next, preparations of 4-[trans-4-(trans-4-alkylcyclohexyl)cyclohexyl]phenols and trans-4-alkyl-4″-hydroxy-trans-octadecahydro-p-terphenyls are shown below.

First, 4-bromoanisole is reacted with metallic Mg to obtain 4-methoxyphenylmagnesium bromide, which is then reacted with a 4-(trans-4-alkylcyclohexyl)cyclohexanone to obtain a 4-methoxy-[1-hydroxy-4-

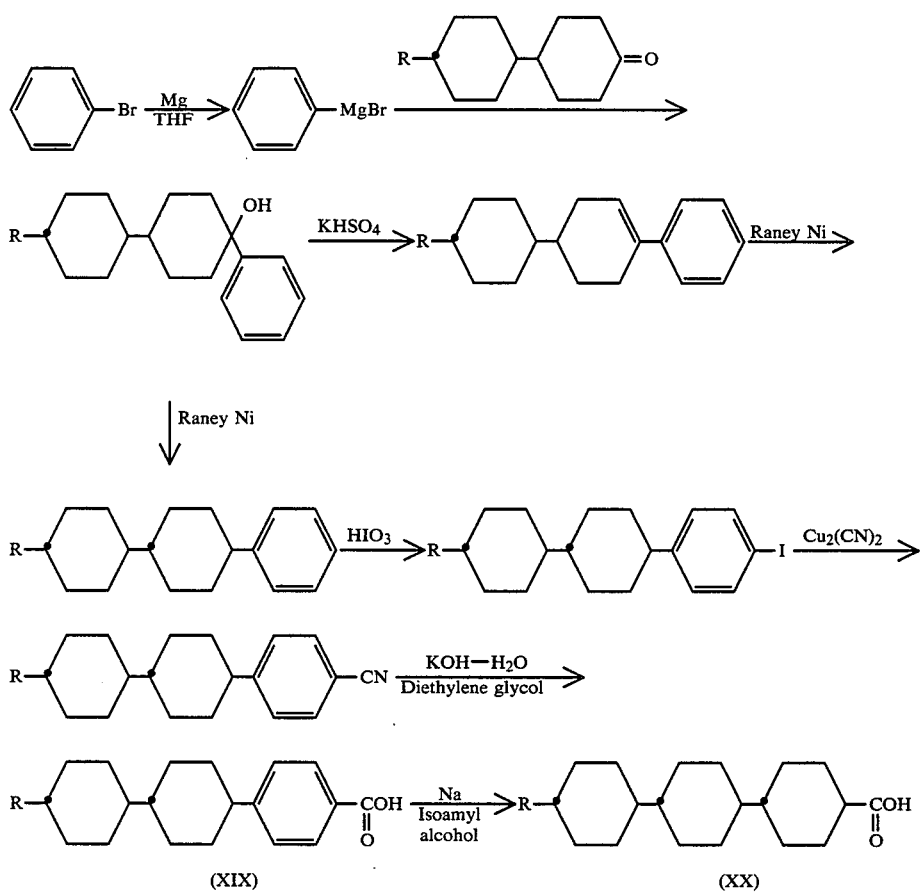

Further, trans-4-[4-(trans-4-alkylcyclohexyl)phenyl]-cyclohexanecarboxylic acids are prepared by reducing 4-(trans-4-alkylcyclohexyl)biphenyl-4-carboxylic acids with metallic sodium in isoamyl alcohol, as in the above reduction from (XIX) into (XX). This preparation is illustrated by the following chemical equation:

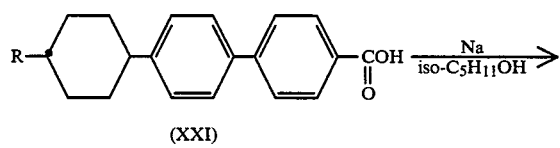

(XXI)

(trans-4″-alkylcyclohexyl)cyclohexyl]benzene, which is then dehydrated in the presence of potassium hydrogen sulfate as a catalyst to obtain a 4-methoxy-[4-(trans-4-alkylcyclohexyl)cyclohexen-1-yl]benzene, which is then reduced with Raney Ni as a catalyst in ethanol solvent under the atmospheric pressure at 30° C. to obtain a 4-methoxy-[4-(trans-4-alkylcycolohexyl)cyclohexyl]benzene which is a mixture of trans-form and cis-form and recrystallized from ethanol to obtain a 4-methoxy-[trans-4-(trans-4-alkylcyclohexyl)cyclohexyl]benzene, wnhich is then demethylated with hydrobromic acid to obtain a 4-[trans-4-(trans-4-alkylcyclohexyl)cyclohexyl]phenol (XXIII), which is then subjected to catalytic reduction in the presence of ruthenium as a catalyst in ethanol solvent at 180° C. under 50 kg/cm² to obtain a trans-4-alkyl-trans-4''-hydroxy-trans-octadecahydro-p-terphenyl (XXIV). The above preparations are illustrated by the following chemical equations:

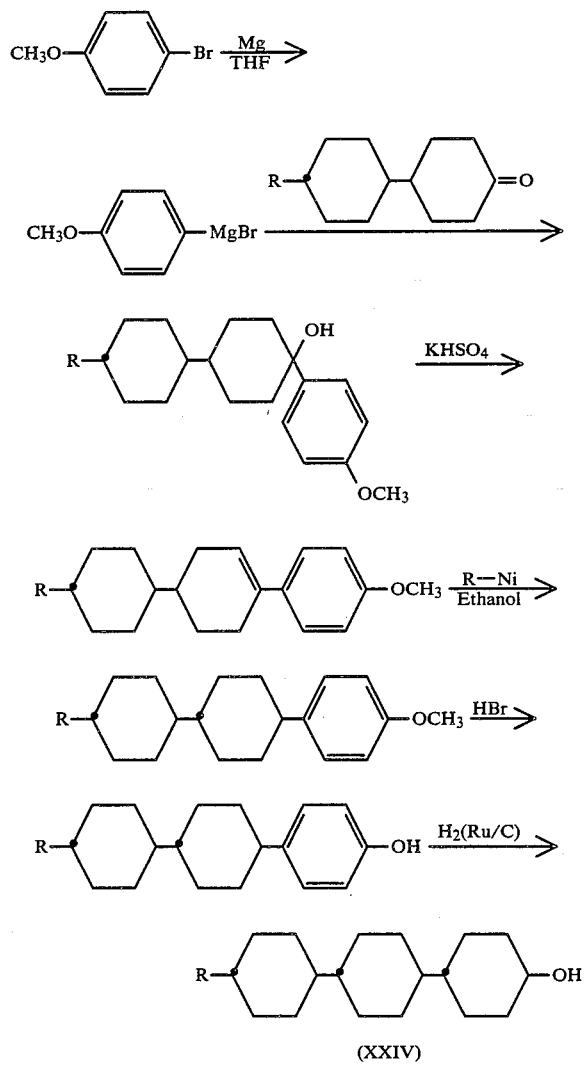

(XXIV)

Among the compounds having 3 six-member-rings, prepared as above, carboxylic acid compounds are converted into acid chlorides with thionyl chloride or the like, which is then subjected to esterification with a commercially available phenol corresponding to the final objective compound, in a conventional manner to obtain the objective ester compounds ((II)∼(XII)). Further, phenols having 3 six-member-rings are subjected to esterification with a commercially available acid chloride corresponding to the objective compound in a conventional manner to obtain the objective ester compounds ((XIII)∼(XVIII)). The above preparations are illustrated by the following chemical equations:

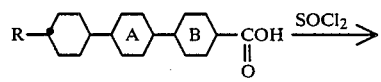

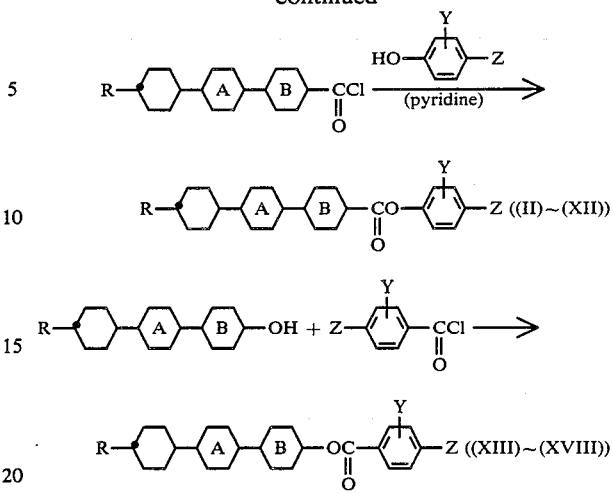

The methods for preparing the compounds of the present invention and the use examples of the compounds as applied to liquid-crystalline compositions will be described by way of Examples.

EXAMPLE 1

Preparation of trans-4''-propyl-trans-octadecahydro-p-terphenyl-trans-4-carboxylic acid-4-fluorophenyl ester (compound of the formula (II) wherein R=C₃H₇ and Z=F)

Sliced Mg (3.6 g, 0.148 mol) was introduced into a three-neck flask and a solution (50 ml) obtained by dissolving bromobenzene (23.2 g, 0.148 mol) in tetrahydrofuran was slowly dropwise added with stirring at a reaction temperature kept at 30° to 35° C. in N₂ current, during which reaction occurred and Mg uniformly dissolved after 3 hours to form phenylmagnesium bromide, to which a solution (50 ml) obtained by dissolving 4-(trans-4-propylcyclohexyl)cyclohexanone (26.2 g, 0.118 mol) in tetrahydrofuran was dropwise added as rapidly as possible at a reaction temperature kept at 10° C. or lower, followed by raising the temperature up to 35° C., stirring for 30 minutes, adding 3N hydrochloric acid (100 ml), transferring the reaction liquid into a separating funnel, three times extracting with n-heptane (100 ml), combining the n-heptane layers, washing with water till the washing liquid became neutral, distilling off n-heptane under reduced pressure to obtain as a residual oily substance, [4-(trans-4-propylcyclohexyl)-cyclohexyl)cyclohexan-1-ol]benzene, adding potassium hydrogen sulfate (19 g) to this material, dehydrating at 170° C. for 2 hours in N₂ current, cooling, adding n-heptane (200 ml), filtering off potassium hydrogen sulfate in a separating funnel, water-washing n-heptane layer till the washing liquid became neutral, distilling off n-heptane under reduced pressure, recrystalling the resulting residual oily substance from n-heptane and acetone to obtain [4-(trans-4-propylcyclohexyl)cyclohexen-1-yl]benzene, dissolving this material (7.5 g) in ethanol (500 ml), adding Raney Ni (3.2 g) as a catalyst, carrying out catalytic reduction at 50° C. under the atmospheric pressure while passing hydrogen, tracing both the raw material and the product by gas chromatography, having the reduction reaction completed when the raw material disappeared, i.e. after 8 hours, to obtain an amount of hydrogen absorbed of 800 ml at that time, filtering off the catalyst, distilling off the solvent under reduced pressure, recrystallizing the residual crystals from ethanol to obtain [trans-4-(trans-4-propylcyclohexyl)cyclohexyl]benzene, dissolving this material (1.4 g) in acetic acid (50 ml), adding a mixture of purified water (0.9 ml), conc. sulfuric acid (1.0 ml), iodic acid (0.20 g), iodine (0.50 g) and CCl₄ (0.4 ml), refluxing at 80° C. for 5 hours, cooling the reaction liquid, filtering off deposited crystals and recrystallizing the crystals from n-heptane to obtain 4-[trans-4-(trans-4-propylcyclohexyl)cyclohexyl]iodobenzene exhibiting a liquid-crystalline state and having a C-S point of 119.0° C., a S-N point of 139.2° C. and a N-I point of 189.2° C. This material (1.2 g) was dissolved in N,N-dimethylformamide (50 ml), followed by adding Cu₂(CN)₂ (0.63 g) to the solution, reacting at 130° C. for 4 hours, adding n-heptane (100 ml), transferring the mixture into a separating funnel, adding 30% aqueous ammonia, to effect liquid-separation, washing with water, washing with 6N hydrochloric acid, washing with water till the washing liquid became neutral, distilling off the solvent under reduced pressure and recrystallizing from n-heptane to obtain 4-[trans-4-(trans-4-propylcyclohexyl)cyclohexyl]benzonitrile (yield: 0.4 g, 45% relative to the cyanogenation reaction; C-S point, 73.1° C.; S-N point, 81.1° C.; N-I point, 242.5° C.).

The thus obtained benzonitrile (5 g) together with a solution obtained by dissolving KOH (5 g) in water (10 ml) were added to diethylene glycol (100 ml) and the mixture was heated and reacted at 200° C. for 7 hours in a flask, followed by cooling down to room temperature, adding 6N HCl (50 ml) and water (100 ml), filtering off deposited crystals, sufficiently washing with water to obtain 4-[trans-4-(trans-4-propylcyclohexyl)cyclohexyl]benzoic acid (XIX), agitating this material (3 g) together with isoamyl alcohol (1500 ml), heating up to 90° C., adding metallic Na (10 g) to initiate vigorous reaction, further adding metallic Na (80 g) over 3 hours still under reflux, to form a uniform reaction liquid gradually, allowing the liquid to cool down to 100° C., distilling off isoamyl alcohol while adding water small-portionwise (the total amount of water added: 1.5 l), adding 6N HCl (1 l) to completely acidify the resulting material, filtering off the resulting precipitate, sufficiently washing with water and recrystallizing from acetic acid to obtain trans-4″-propyl-trans-octadecahydro-p-terphenyl-trans-4-carboxylic acid (XX) (yield: 1.9 g, 63%). This product also exhibited a liquid-crystallanity and had a C-S point of ca. 170° C., a S-N point of 282° C. and a N-I point of 290°∼300° C. (accompanied with decomposition)

The thus prepared carboxylic acid (0.5 g) together with thionyl chloride (10 ml) were heated to 80° C. for 2 hours for reaction to form a uniform reaction liquid, and the reaction was continued further for 1.5 hour, followed by distilling off excess thionyl chloride under reduced pressure to obtain an acid chloride as a residual oily substance. To this acid chloride was added a solution obtained by dissolving 4-fluorophenol (0.5 g) in pyridine (20 ml), followed by adding toluene (100 ml), allowing the mixture to stand over night, washing the toluene layer in a separating funnel first with 6N HCl, then with 2N NaOH solution and lastly with water till the washing liquid became neutral, drying with anhydrous sodium sulfate, distilling off toluene under reduced pressure and recrystallizing deposited crystals from ethanol and then from acetone to obtain the objective trans-4″-propyl-trans-octadecahydro-p-terphenyl-trans-4-carboxylic acid-4-fluorophenyl ester (yield, 0.4 g, 62%; C-S point, 94.0° C.; S-N point, 220.6° C.; N-I point, 300° C. or higher).

EXAMPLES 2∼21

In Example 1, 4-(trans-4-propylcyclohexyl)cyclohexanone was replaced by 4-(trans-4-alkylcyclohexyl)cyclohexanones having other alkyl groups to prepare 4-[trans-4-(trans-4-alkylcyclohexyl)cyclohexyl]benzoic acids and trans-4″-alkyl-trans-octahydro-p-terphenyl-trans-4-carboxylic acids. These compounds were converted with 4-fluorophenol, instead other halogenophenols or 4-cyanophenol into the objective compounds expressed by the formulas (II), (III), (V), (VI), (IX) and (X). The results are shown in Table 1 together with those of Example 1.

TABLE 1

| | In formula (I) | | | | Phase transition point (°C.) | | | |
| --- | --- | --- | --- | --- | --- | --- | --- | --- |
| Example | R | -B- | Y | Z | C-S point or C-N point | S-N point | N-I point | Formula |
| 1 | C₃H₇ | cyclohexyl | H | F | 94.0 | 220.6 | 300 or higher | (II) |
| 2 | C₃H₇ | cyclohexyl | H | Cl | 106.0 | 158.1 | 296.6 | ″ |
| 3 | C₃H₇ | cyclohexyl | H | CN | 119.0 | 194.3 | 300 or higher | ″ |
| 4 | H | phenyl | H | F | 147.2 | — | 168.9 | (III) |
| 5 | C₃H₇ | phenyl | H | F | 108.2 | — | 300 or higher | ″ |
| 6 | H | phenyl | H | Cl | 152.8 | — | 192.0 | ″ |

TABLE 1-continued

| Example | R | B (in formula I) | Y | Z | C-S point or C-N point | S-N point | N-I point | Formula |
|---|---|---|---|---|---|---|---|---|
| 7 | $C_3H_7$ | cyclohexyl | H | Cl | 134.5 | — | 300 or higher | " |
| 8 | H | cyclohexyl | H | CN | 151.6 | — | 230.0 | " |
| 9 | $C_3H_7$ | cyclohexyl | H | CN | 162.7 | — | 300 or higher | " |
| 10 | $C_3H_7$ | cyclohexyl | 2-Cl* | F | 92.0 | 190.1 | 256.3 | (V) |
| 11 | $C_3H_7$ | cyclohexyl | 2-F | Cl | 98.0 | 192.0 | 285.0 | " |
| 12 | $C_3H_7$ | cyclohexyl | 2-Cl | Cl | 103.0 | 134.0 | 260.7 | " |
| 13 | $C_3H_7$ | cyclohexyl | 3-Cl | F | 84.0 | 162.4 | 265.3 | (IX) |
| 14 | $C_3H_7$ | cyclohexyl | 3-Cl | Cl | 107.0 | 123.2 | 268.0 | " |
| 15 | H | phenyl | 2-Cl | F | 102.0 | — | — | (VI) |
| 16 | H | phenyl | 2-F | Cl | 98.0 | — | — | " |
| 17 | $C_3H_7$ | phenyl | 2-Cl | F | 77.0 | — | 231.0 | " |
| 18 | $C_3H_7$ | phenyl | 2-F | Cl | 74.0 | — | 233.0 | " |
| 19 | $C_3H_7$ | phenyl | 2-Cl | Cl | 76.0 | — | 228.0 | " |
| 20 | $C_3H_7$ | phenyl | 3-Cl | F | 124.7 | — | 242.3 | (X) |
| 21 | $C_3H_7$ | phenyl | 3-Cl | Cl | 126.3 | — | 287.8 | " |

*The numeral before the name of halogen refers to the position of halogen attached onto benzene ring.

EXAMPLE 22

Preparation of trans-4-[4-(trans-4-pentylcyclohexyl)phenyl]cyclohexanecarboxylic acid-4-fluorophenyl ester (a compound of the formula (IV) wherein R=$C_5H_{11}$ and Z=F) 4-(Trans-4-pentylcyclohexyl)biphenyl-4-carboxylic acid (XXI) (10 g) together with isoamyl alcohol (2,500 ml) were heated to 90° C. with stirring, followed by adding metallic Na (30 g) with a vigorous reaction being initiated, further adding metallic Na (120 g) over 3 hours while still continuing reflux to gradually form a uniform reaction liquid, allowing the liquid after the reaction to cool down to 100° C., distilling off isoamyl alcohol while adding water (2,000 ml), adding 6N HCl (2 l) for complete acidification, filtering off deposited precipitate, washing with water and recrystallizing from acetic acid to obtain trans-4-[4-(trans-4-pentylcyclohexyl)phenyl]cyclohexanecarboxylic acid (XXII) (4.5 g), which exhibited a liquid-crystallinity and had a C-S point of 239.1° C. and a S-I point of 274.3° C. (decomposition).

This carboxylic acid (1 g) together with thionyl chloride (30 ml) were heated to 80° C. for reaction to form a uniform reaction liquid in 2 hours, followed by continuing reaction further for 1.5 hour, distilling off excess thionyl chloride under reduced pressure to obtain an acid chloride as a residual oily substance, adding to this acid chloride, a solution obtained by dissolving 4-fluorophenol (0.5 g) in pyridine (20 ml), adding toluene (100 ml), allowing the mixture to stand over night, washing the toluene layer in a separating funnel first with 6N HCl, then with 2N NaOH solution and finally with water till the washing liquid became neutral, drying with anhydrous $NaSO_4$, distilling off the toluene layer under reduced pressure and recrystallizing deposited crystals from ethanol and then from acetone to prepare the objective trans-4-[4-(trans-4-pentylcyclohexyl)phenyl]cyclohexanecarboxylic acid-4-fluorophenyl ester (yield; 0.5 g, 40%, C-S point, 100.1° C.; S-N point, 152.2° C.; N-I point, 261.0° C.). The fact that this compound corresponded to the objective substance was confirmed by infrared absorption spectra and NMR.

EXAMPLE 23

In Example 22, trans-4-[4-(trans-4-pentylcyclohexyl)phenyl]cyclohexanecarboxylic acid was replaced by trans-4-[4-(trans-4-alkylcyclohexyl)phenyl]cyclohexanecarboxylic acids having other alkyl groups or 4'-(trans-4-alkylcyclohexyl)biphenyl-4-carboxylic acid, and also fluorophenol, instead other halogenophenols or 4-cyanophenyl was used to prepare the objective compounds expressed by the formulas (IV), (VII), (VIII), (XI) and (XII). The results are shown in Table 2 together with those of Example 22.

TABLE 2

| | | In formula (I) | | | Phase transition point (°C.) | | | |
|---|---|---|---|---|---|---|---|---|
| Example | R | —⟨B⟩— | Y | Z | C-S point or C-N point | S-N point | N-I point | Formula |
| 22 | $C_5H_{11}$ |  | H | F | 100.1 | 152.2 | 261.0 | (IV) |
| 23 | $C_5H_{11}$ |  | H | Cl | 120.3 | 129.3 | 264.3 | " |
| 24 | $C_5H_{11}$ |  | H | CN | 110.5 | — | 284.9 | " |
| 25 | $C_5H_{11}$ |  | Cl | F | 83.0 | — | 237.8 | (VII) |
| 26 | $C_5H_{11}$ |  | F | Cl | 106.1 | 144.0 | 263.6 | " |
| 27 | $C_5H_{11}$ |  | Cl | Cl | 112.0 | — | 241.7 | " |
| 28 | $C_5H_{11}$ |  | 3-Cl | F | 104.8 | — | 214.7 | (XI) |
| 29 | $C_5H_{11}$ |  | 3-Cl | Cl | 88.8 | — | 223.2 | " |
| 30 | $C_5H_{11}$ |  | 2-Cl | F | 74.1 | 106.4 | 279.6 | (VIII) |
| 31 | $C_5H_{11}$ |  | 2-F | Cl | 125.1 | 218.0 | 300 or higher | " |
| 32 | $C_5H_{11}$ |  | 2-Cl | Cl | 101.0 | (95.0) | 299.0 | " |

TABLE 2-continued

| | | In formula (I) | | | Phase transition point (°C.) | | | |
|---|---|---|---|---|---|---|---|---|
| Example | R | —B— | Y | Z | C-S point or C-N point | S-N point | N-I point | Formula |
| 33 | $C_5H_{11}$ | (phenyl) | 3-Cl | F | 109.5 | 182.6 | 256.6 | (XII) |
| 34 | $C_5H_{11}$ | (phenyl) | 3-Cl | Cl | 116.0 | 196.7 | 266.8 | " |

EXAMPLE 35

Preparation of trans-4-propyl-trans-4'-(4-fluorobenzoyloxy)-octadecahydro-trans-p-terphenyl (a compound of the formula (XIII) wherein R=$C_3H_7$ and Z=F)

Sliced Mg (1.2 g, 0.049 mol) was introduced into a three-neck flask and a solution (30 ml) obtained by dissolving 4-bromoanisole (9.2 g, 0.049 mol) in tetrahydrofuran was slowly dropwise added with stirring at a reaction temperature kept at 30° to 35° C. in $N_2$ current, during which reaction occurred and Mg uniformly dissolved in 3 hours to form 4-methoxy-phenylmagnesium bromide, to which a solution (50 ml) obtained by dissolving 4-(trans-4-propylcyclohexy)cyclohexanone (10.9 g, 0.049 mol) in tetrahydrofuran was dropwise added as rapidly as possible at a reaction temperature kept at a reaction temperature of 5° to 10° C., followed by raising the temperature up to 35° C., stirring for 30 minutes, adding 3N hydrochloric acid (50 ml), transferring the reaction liquid into a separating funnel, three times extracting with toluene (200 ml), combining the toluene layers, washing with water till the washing liquid became neutral, distilling off toluene under reduced pressure to obtain as a residual oily substance, 4-methoxy-[1-hydroxy-4-(trans-4-propylcyclohexyl)cyclohexyl]benzene, adding potassium hydrogen sulfate (6 g) to this material, dehydrating at 160° C. for 2 hours in $N_2$ current, cooling, adding toluene (200 ml), filtering off potassium hydrogen sulfate, water-washing toluene layer till the washing liquid became neutral, distilling off toluene under reduced pressure, recrystalling the resulting residual oily substance from ethanol to obtain 4-methoxy-[4-(trans-4-propylcyclohexyl)cyclohexen-1-yl]benzene, dissolving the total amount of this material (7.0 g) in ethanol (120 ml) together with Raney Ni (1.0 g), carrying out catalytic reduction at 50° C. under the atmospheric pressure, to have 500 ml of hydrogen absorbed, filtering off the catalyst, recrystallizing as it was, to obtain a mixture of cis-form and trans-form, repeatedly recrystallizing to isolate the trans-form which was 4-methoxy-[trans-4-(trans-4-propylcyclohexyl)cyclohexyl]benzene (yield: 28 g, 18%).

This material (15 g) together with hydrobromic acid (47%) (200 ml) and acetic acid (200 ml) were refluxed for 20 hours for reaction, followed by adding water (500 ml), filtering off deposited crystals, sufficiently washing with water and recrystallizing from a mixed solvent of acetone-ethanol to obtain 4-[trans-4-(trans-4-propylcyclohexyl)cyclohexyl]phenol (XXIII) (yield: 11 g, 77%).

The thus prepared 4-[trans-4-(trans-4-propylcyclohexyl)cyclohexyl]phenyl (8 g) was dissolved in ethanol (400 ml), followed by adding Ru/C catalyst (1.0 g), carrying out catalytic reduction at 180° C., under 50 kg/cm² for 5 hours, filtering off the catalyst, distilling off the solvent under reduced pressure and recrystallizing the residual crystals from acetone (1 l) to obtain trans-4-propyl-trans-4''-hydroxy-octadecahydro-trans-p-terphenyl (XXIV) (yield: 3.8 g, 47%, m.p.: 232°~237° C.). This material (1 g) was dissolved in pyridine (50 ml) and to the solution was added 4-fluorobenzoic acid chloride (1 g), followed by allowing the mixture to stand over night, adding toluene (200 ml), washing the toluene layer in a separating funnel first with 6N HCl, then with 2N NaOH solution and finally with water till the washing liquid became neutral, drying with anhydrous $Na_2SO_4$, distilling off the toluene layer under reduced pressure and recrystallizing deposited crystals from acetone to obtain the objective trans-4-propyl-trans-4''-(4-fluorobenzoyloxy)-octadecahydro-trans-p-terphenyl (yield: 0.8 g, 57%, C-S point: 102° C., S-N point: 225.8° C., N-I point: 297.0° C.).

EXAMPLES 36~57

In Example 35, trans-4-propyl-trans-4''-hydroxy-octadecahydro-trans-p-terphenyl was replaced by trans-4-alkyl-trans-4''-hydroxyoctadecahydro-trans-p-terphenyls having other alkyl groups (XXIV) or 4-[trans-4-(trans-4-alkylcyclohexyl)cyclohexyl]phenols (XXIII), and also 4-fluorobenzoic acid chloride, instead other halogenobenzoic acid chlorides or 4-cyanobenzoic acid chloride were used to prepare the objective compounds expressed by the formulas (XIII), (XIV), (XV), (XVI), (XVII) and (XVIII). The results are shown in Table 3 together with those of Example 35.

TABLE 3

| | | In formula (I) | | | Phase transition point (°C.) | | | |
|---|---|---|---|---|---|---|---|---|
| Example | R | —B— | Y | Z | C-S point or C-N point | S-N point | N-I point | Formula |
| 35 | $C_3H_7$ | (cyclohexyl) | H | F | 102.0 | 225.8 | 297.0 | (XIII) |
| 36 | $C_4H_9$ | (cyclohexyl) | H | F | 87.0 | 217.8 | 274.0 | " |

TABLE 3-continued
| Example | In formula (I) R | B | Y | Z | C-S point or C-N point | S-N point | N-I point | Formula |
|---|---|---|---|---|---|---|---|---|
| 37 | $C_7H_{15}$ |  | H | F | 72.0 | 235.0 | 258.1 | " |
| 38 | $C_7H_{15}$ |  | H | Cl | 8032 | 226.0 | 279.5 | " |
| 39 | $C_3H_7$ |  | H | CN | 159.0 | 204.3 | 300 or higher | " |
| 40 | $C_4H_9$ |  | H | CN | 151.8 | 209.2 | 300 or higher | " |
| 41 | $C_7H_{15}$ |  | H | CN | 147.3 | 214.5 | 298.1 | " |
| 42 | $C_3H_7$ |  | 2-Cl | Cl | 98.0 | 190.1 | 273.5 | (XV) |
| 43 | $C_4H_9$ |  | 2-Cl | Cl | 86.0 | 212.2 | 285.0 | " |
| 44 | $C_7H_{15}$ |  | 2-Cl | Cl | 90.0 | 216.3 | 268.6 | " |
| 45 | $C_3H_7$ |  | 3-Cl | Cl | 139.5 | 159.4 | 269.6 | (XVII) |
| 46 | $C_4H_9$ |  | 3-Cl | Cl | 114.0 | 189.4 | 267.1 | " |
| 47 | $C_7H_{15}$ |  | 3-Cl | Cl | 107.5 | 210.9 | 268.4 | " |
| 48 | $C_3H_7$ |  | H | F | 107.0 | 195.8 | 300 or higher | (XIV) |
| 49 | $C_4H_9$ |  | H | F | 115.0 | 204.3 | 275.8 | " |
| 50 | $C_3H_7$ |  | H | Cl | 141.0 | 201.6 | 300 or higher | " |
| 51 | $C_4H_9$ |  | H | Cl | 140.0 | 179.7 | 300 or higher | " |
| 52 | $C_3H_7$ |  | H | CN | 215.0 | — | 300 or higher | " |
| 53 | $C_4H_9$ |  | H | CN | 206.0 | — | 300 or higher | " |
| 54 | $C_3H_7$ |  | 2-Cl | Cl | 108.9 | 114.2 | 279.9 | (XVI) |
| 55 | $C_4H_9$ |  | 2-Cl | Cl | 81.9 | 136.7 | 289.6 | " |

TABLE 3-continued

| | In formula (I) | | | | Phase transition point (°C.) | | | |
|---|---|---|---|---|---|---|---|---|
| Example | R | —⟨B⟩— | Y | Z | C-S point or C-N point | S-N point | N-I point | Formula |
| 56 | $C_3H_7$ | —⟨ ⟩— | 3-Cl | Cl | 145.0 | 185.0 | 300 or higher | (XVIII) |
| 57 | $C_4H_9$ | —⟨ ⟩— | 3-Cl | Cl | 137.1 | 197.5 | 300 or higher | " |

EXAMPLE 58 (USE EXAMPLE)

A liquid-crystalline composition (A) consisting of trans-4-propyl-(4'-cyanophenyl)cyclohexane (28% by weight), trans-4-pentyl-(4'-cyanophenyl)cyclohexane (42% by weight), trans-4-heptyl-(4'-cyanophenyl)cyclohexane (30% by weight), had a nematic-clearing point of 52° C. When this liquid-crystalline composition was sealed in a TN cell (twisted, nematic cell) of 10 μm thick, the resulting cell has an actuation threshold voltage of 1.53 V and a saturation voltage of 2.12 V. Its viscosity was 23 cp at 20° C. and its optical anisotropy value was 0.120.

When trans-4"-propyl-trans-octadecahydro-p-terphenyl-trans-4-carboxylic acid-4-fluorophenyl ester (3 parts by weight) ("parts by weight" hereinafter being abbreviated to parts) prepared in Example 1 was added to the above liquid-crystalline composition (A) (97 parts), the resulting nematic composition had a nematic-clearing point of 60° C. The threshold voltage and saturation voltage were 1.50 V and 2.09 V, respectively. Its viscosity was 23 cp at 20° C.

EXAMPLE 59 (USE EXAMPLE)

A liquid-crystalline composition obtained by adding 4-[trans-4-(trans-4-propylcyclohexyl)cyclohexyl]-benzoic acid-4-fluorophenyl ester (5 parts) prepared in Example 5 to the liquid-crystalline composition (A) (95 parts) had a nematic-clearing point of 65° C. The threshold voltage and saturation voltage were 1.55 V and 2.14 V, respectively. Its viscosity was 25 cp at 20° C.

EXAMPLE 60 (USE EXAMPLE)

A liquid-crystalline composition obtained by adding trans-4-[4-(trans-4-pentylcyclohexyl)phenyl]-cyclohexanecarboxylic acid-4-fluorophenyl ester (5 parts) prepared in Example 22 to that liquid-crystalline composition (A) (95 parts) had a N-I point of 62.4° C. The values of the threshold voltage and saturation voltage measured as above were 1.55 V and 2.14 V, respectively. Its viscosity was 24 cp at 20° C. and its optical anisotropy value was 0.120, that is, almost unchanged.

EXAMPLE 61 (USE EXAMPLE)

A nematic composition obtained by adding trans-4"-propyl-trans-octadecahydro-p-terphenyl-trans-4-carboxylic acid-2-chloro-4-fluorophenyl ester (3 parts) prepared in Example 10 to the liquid-crystalline composition (A) (97 parts) had a nematic-clearing point of 58° C. The threshold voltage and saturation voltage were 1.50 V and 2.09 V, respectively. Its viscosity was 24 cp at 20° C.

EXAMPLE 62 (USE EXAMPLE)

A liquid-crystalline composition obtained by adding 4-[trans-4-(trans-4-propylcyclohexyl)cyclohexyl]-benzoic acid-2-chloro-4-fluorophenyl ester (3 parts) prepared in Example 17 to the liquid-crystalline composition (A) (97 parts) had a N-I point elevated to 57° C. The threshold voltage and saturation voltage were 1.54 V and 2.15 V, respectively, and its viscosity was 24 cp at 20° C., that is, these values only slightly rised, respectively.

EXAMPLE 63 (USE EXAMPLE)

A liquid-crystalline composition obtained by adding trans-4-[4-(trans-4-pentylcyclohexyl)phenyl]-cyclohexanecarboxylic acid-2-chloro-4-fluorophenyl ester (5 parts) prepared in Example 25 to the liquid-crystalline composition (A) (95 parts) had a N-I point of 61° C. The values of the threshold voltage and saturation voltage measured above were 1.55 V and 2.14 V, respectively. Its viscosity was 24 cp at 20° C. and its optical anisotropy value was 0.120, that is, these values were almost unchanged.

EXAMPLE 64 (USE EXAMPLE)

A liquid-crystalline composition (B) consisting of
4-pentyl-4'-cyanobiphenyl (45% by weight),
4-heptyl-4'-cyanobiphenyl (29% by weight),
4-octyloxy-4'-cyanobiphenyl (15% by weight) and
4-phenyl-4'-cyanoterphenyl (11%)
has a N-I point of 63.3° C., a viscosity of 46 cp at 20° C. and a dielectric anisotropy of +12.4. This liquid-crystalline composition was sealed in a cell of 10 μm thick composed of two base plates provided with transparent tin oxide electrodes coated with $SiO_2$ and subjected to rubbing treatment to prepare a liquid-crystalline cell. Its characteristics properties were measured at 25° C. to give a threshold voltage of 1.65 V and a saturation voltage of 2.31 V.

A composition obtained by adding 4'-(trans-4-pentylcyclohexyl)biphenyl-4-carboxylic acid-2-chloro-4-fluorophenyl ester (5 parts) of Example 30 of the present invention to the liquid-crystalline composition (B) (95 parts) had a N-I point raised to 74° C. Its viscosity was 45 cp at 20° C. and its dielectric anisotropy value was +10.5, that is, these values were reduced. Further the threshold voltage and saturation voltage were 1.60 V and 2.20 V, respectively, that is, these values were also reduced.

EXAMPLE 65 (USE EXAMPLE)

A nematic composition obtained by adding trans-4"-propyl-trans-octadecahydro-p-terphenyl-trans-4-carboxylic acid-2-chloro-4-fluorophenyl ester (3 parts)

prepared in Example 13 to the liquid-crystalline composition (A) (97 parts) had a nematic-clearing point of 58° C., a threshold voltage of 1.49 V and a saturation voltage of 2.09 V. Its viscosity was 24 cp at 20° C.

EXAMPLE 66 (USE EXAMPLE)

A composition obtained by adding 4-[trans-4-(trans-4-propylcyclohexyl)cyclohexyl]benzoic acid-3-chloro-4-fluorophenyl ester (3 parts) prepared in Example 20 to the liquid-crystalline composition (A) (97 parts) had a N-I point of 56° C., a threshold voltage of 1.55 V and a saturation voltage of 2.14 V. Its viscosity was 25 cp at 20° C.

EXAMPLE 67 (USE EXAMPLE)

A liquid-crystalline composition obtained by adding trans-4-[4-(trans-4-pentylcyclohexyl)phenyl]cyclohexanecarboxylic acid-3-chloro-4-fluorophenyl ester (5 parts) prepared in Example 28 to the liquid-crystalline composition (A) (95 parts) had a N-I point of 60° C. The threshold voltage and saturation voltage measured as above were 1.55 V and 2.14 V, respectively. Its viscosity was 24 cp at 20° C. and its optical anisotropy value was 0.120, that is, almost unchanged.

EXAMPLE 68 (USE EXAMPLE)

A composition consisting of the liquid-crystalline composition (B) (97 parts) and 4'-(trans-4-pentylcyclohexyl)biphenyl-4-carboxylic acid-3-chlor-4-fluorophenyl ester (3 parts) prepared in Example 33 had a N-I point raised to 69° C. Its viscosity was 47 cp at 20° C. and its dielectric anisotropy value was +10.5, that is, these values were reduced. Further, the threshold voltage and saturation voltage were 1.60 V and 2.20 V, respectively, that is, these values were also reduced.

EXAMPLE 69 (USE EXAMPLE)

A nematic composition obtained by adding trans-4''-propyl-trans-3-octadecahydro-p-terphenyl-trans-4-carboxylic acid-4-cyanophenyl ester (3 parts) prepared in Example 3 to the liquid-crystalline composition (A) (97 parts) had a nematic-clearing point of 61° C., a threshold voltage of 1.54 V and a saturation voltage of 2.13 V. Its viscosity was 25 cp at 20° C.

EXAMPLE 70 (USE EXAMPLE)

A composition obtained by adding 4-[trans-4-propylcyclohexyl)cyclohexyl]benzoic acid-4-cyanophenyl ester (2 parts) prepared in Example 9 to the liquid-crystalline composition (A) (98 parts) had a nematic-clearing point of 58° C., a threshold voltage of 1.55 V and a saturation voltage of 2.14 V. Its viscosity was 25 cp at 20° C.

EXAMPLE 71 (USE EXAMPLE)

A liquid-crystalline composition obtained by adding trans-4-[4-(trans-4-pentylcyclohexyl)phenyl]-cyclohexanecarboxylic acid-4-cyanophenyl ester (3 parts) prepared in Example 24 to the liquid-crystalline composition (A) (97 parts) had a N-I point of 59° C. The threshold voltage and saturation voltage measured as above were 1.54 V and 2.13 V, respectively. Its viscosity was 24 cp at 20° C. and its optical anisotropy value was 0.120, that is, these values were almost unchanged.

EXAMPLE 72 (USE EXAMPLE)

A liquid-crystalline composition obtained by adding trans-4-propyl-trans-4''-(4-fluorobenzyloxy)-octadecahydro-trans-p-terphenyl (3 parts) prepared in Example 35 to the liquid-crystalline composition (A) (97 parts) had a N-I point raised to 58° C. and when this composition was made up into a TN cell as described above, the threshold voltage and saturation voltage were 1.55 V and 2.14 V, respectively. Its viscosity was 26 cp at 20° C.

EXAMPLE 73 (USE EXAMPLE)

A liquid-crystalline composition obtained by adding trans-4-propyl-trans-4''-(4-cyanobenzoyloxy)-octadecahydro-trans-p-terphenyl (3 parts) prepared in Example 39 to the liquid-crystalline composition (A) (97 parts) had a N-I point raised to 58° C. and when this composition was made up into a TN cell as described above, the threshold voltage and saturation voltage were 1.55 V and 2.14 V, respectively. Its viscosity was 28 cp at 20° C.

EXAMPLE 74 (USE EXAMPLE)

A liquid-crystalline composition obtained by adding 4-fluorobenzoic acid-4-[trans-4-(trans-4-propylcyclohexyl)cyclohexyl]phenyl ester (3 parts) prepared in Example 48 to the liquid-crystalline composition (A) (97 parts) had a N-I point raised to 61° C. and when this composition was made up into a TN cell as described above, the threshold voltage and saturation voltage were 1.55 V and 2.14 V, respectively. Its viscosity was 28 cp at 20° C.

EXAMPLE 75 (USE EXAMPLE)

A liquid-crystalline composition obtained by adding 4-cyanobenzoic acid-4-[trans-4-(trans-4-propylcyclohexyl)cyclohexyl]phenyl ester (2 parts) prepared in Example 52 to the liquid-crystalline composition (A) (98 parts) had a N-I point raised to 59° C. and when this composition was made up into a TN cell as described above, the threshold voltage and saturation voltage were 1.55 V and 2.14 V, respectively. Its viscosity was 29 cp at 20° C.

EXAMPLE 76 (USE EXAMPLE)

A liquid-crystalline composition obtained by adding trans-4-propyl-trans-4''-(2,4-dicyclobenzoyloxy)-octadecahydro-trans-p-terphenyl (3 parts) prepared in Example 42 to the liquid composition (A) (97 parts) had a N-I point raised to 58° C., and when this composition was made up into a TN cell as described above, the threshold voltage and saturation voltage were 1.55 V and 2.14 V, respectively. Its viscosity was 27 cp at 20° C.

EXAMPLE 77 (USE EXAMPLE)

A liquid-crystalline composition obtained by adding 2,4-dichlorobenzoic acid-4-[trans-4-(trans-4-propylcyclohexyl)phenyl ester (3 parts) prepared in Example 54 to the liquid-crystalline composition (A) (97 parts) had a N-I point raised to 58° C., and when this composition was made up into a TN cell as described above, the threshold voltage and saturation voltage were 1.55 V and 2.14 V, respectively. Its viscosity was 28 cp at 20° C.

EXAMPLE 78 (USE EXAMPLE)

A liquid-crystalline composition obtained by adding trans-4-propyl-trans-4''-(3,4-dichlorobenzoyloxy)octadecahydro-trans-p-terphenyl (3 parts) prepared in Example 56 to the liquid-crystalline composition (A)

(97 parts) had a N-I point raised to 58° C., and when this composition was made up into a TN cell as described above, the threshold voltage and saturation voltage were 1.55 V and 2.14 V, respectively. Its viscosity was 27 cp at 20° C.

EXAMPLE 79 (USE EXAMPLE)

A liquid-crystalline composition obtained by adding 3,4-dichlorobenzoic acid-4-[trans-4-(trans-4-propylcyclohexyl)cyclohexyl]phenyl ester (3 parts) prepared in Example 56 to the liquid-crystalline composition (A) (97 parts) had a N-I point raised to 60° C., and when this composition was made up into a TN cell as described above, the threshold voltage and saturation voltage were 1.55 V and 2.14 V, respectively. Its viscosity was 28 cp at 20° C.

What is claimed is:

1. Liquid crystalline ester compounds expressed by the general formula

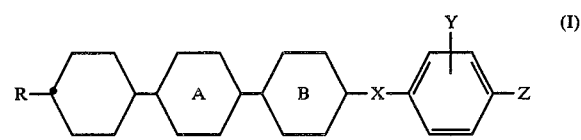
(I)

wherein R represents hydrogen atom or an alkyl group of 1 to 10 carbon atoms;

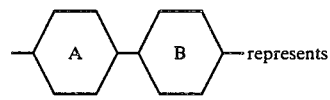 represents

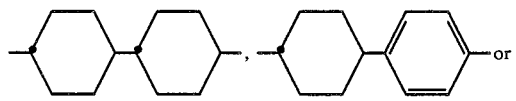

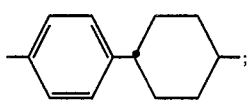

X represents

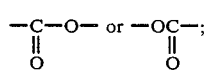

Y is hydrogen, F or Cl; and
Z is F, Cl or CN; with the proviso that when Y is hydrogen then

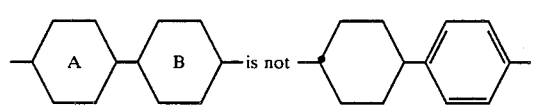

2. Trans-4'-alkyl-trans-octadecahydro-p-terphenyl-trans-4-carboxylic acid-4-substituted phenyl esters expressed by the general formula

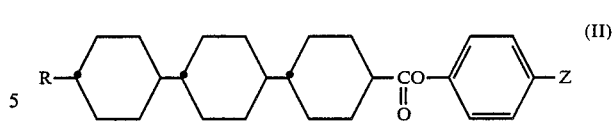
(II)

wherein R and Z each have the same definitions as in claim 1.

3. Compounds as set forth in claim 1 which can be designated as trans-4-[4-(trans-4-alkylcyclohexyl)-phenyl]cyclohexanecarboxylic acid-4-substituted phenyl esters and which is expressed by the general formula

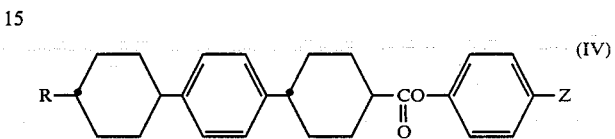
(IV)

wherein R and X each have the same definitions as in claim 1.

4. Compounds as set forth in claim 1 which can be designated as trans-4″-alkyl-trans-octadecahydro-p-terphenyl-trans-4-carboxylic acid-2,4-dihalogenophenyl esters and which can be expressed by the general formula

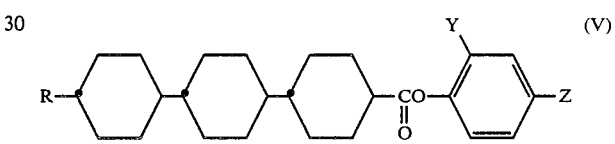
(V)

wherein R has the same definition as in claim 1 and Y and Z each represent F or Cl.

5. Compounds as set forth in claim 1 which can be designated as 4-[trans-4-(trans-4-alkylcyclohexyl)cyclohexyl]benzoic acid-2,4-dihalogenophenyl esters and which can be expressed by the general formula

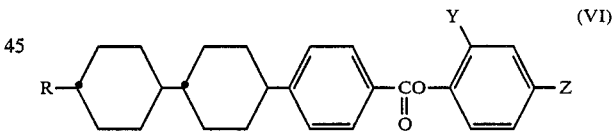
(VI)

wherein R has the same definition as in claim 1 and Y and Z each represent F or Cl.

6. Compounds as set forth in claim 1 which can be designated as trans-4-[-(trans-4-alkylcyclohexyl)-phenyl]cyclohexanecarboxylic acid-2,4-dihalogenophenyl esters and which can be expressed by the general formula

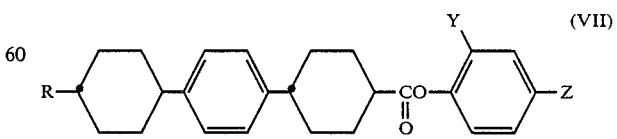
(VII)

wherein R has the same definition as in claim 1 and Y and Z each represent F or Cl.

7. Compounds as set forth in claim 1 which can be designated as 4-(trans-4-alkylcyclohexyl)biphenyl-4- carboxylic acid-2,4-dihalogenophenyl esters and which can be expressed by the general formula

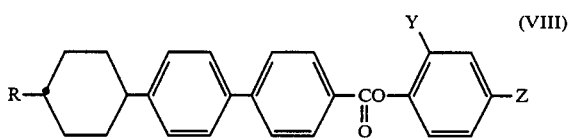

wherein R has the same definition as in claim 1 and Y and Z each represent F or Cl.

8. Compounds as set forth in claim 1 which can be designated as trans-4″-alkyl-trans-octadecahydro-p-terphenyl-trans-4-carboxylic acid-3,4-dihalogeno-phenyl esters expressed by the general formula

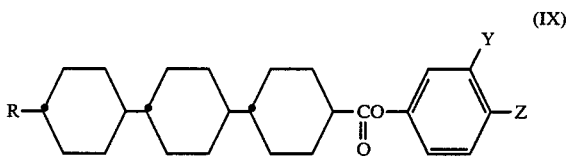

wherein R has the same definition as in claim 1 and Y and Z each represent F or Cl.

9. Compounds as set forth in claim 1 which can be designated as 4-[trans-4-(trans-4-alkylcyclohexyl)cyclohexyl]benzoic acid-3,4-dihalogenophenyl esters and which can be expressed by the general formula

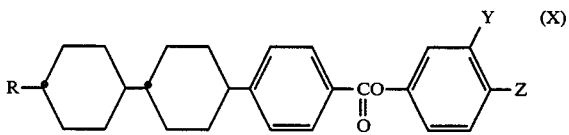

wherein R has the same definition as in claim 1 and Y and Z each represent F or Cl.

10. Compounds as set forth in claim 1 which can be designated as trans-4-[4-(trans-4-alkylcyclohexyl)phenyl]cyclohexanecarboxylic acid-3,4-dihalogenophenyl esters and which can be expressed by the general formula

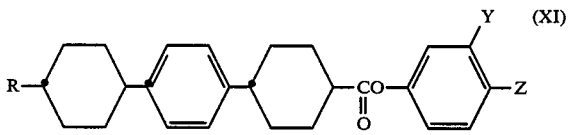

wherein R has the same definition as in claim 1 and Y and Z each represent F or Cl.

11. Compounds as set forth in claim 1 which can be designated as trans-4-alkyl-trans-4″-(4-substituted benzoyloxy)octadecahydro-trans-p-terphenyls and which can be expressed by the general formula

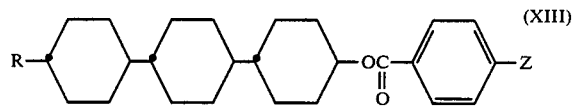

wherein R has the same definition as in claim 1 and Z represents F, Cl or CN.

12. Compounds as set forth in claim 1 which can be designated as trans-4-alkyl-trans-4″-(2,4-dichlorobenzoyloxy)octadecahydro-trans-p-terphenyls and which can be expressed by the formula

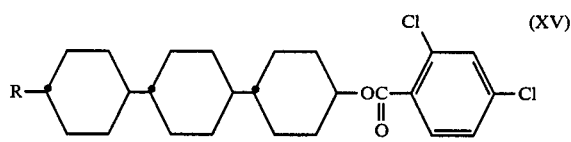

wherein R has the same definition as in claim 1.

13. Compounds as set forth in claim 1 which can be designated as 2,4-dichlorobenzoic acid-4-[trans-4-(trans-4-alkylcyclohexyl)cyclohexyl]phenyl esters and which can be expressed by the general formula

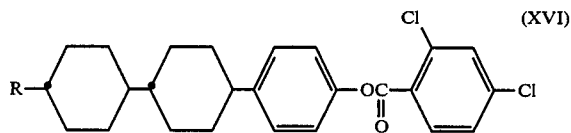

wherein R has the same definition as in claim 1.

14. Compounds as set forth in claim 1 which can be designated as trans-4-alkyl-trans-4″-(3,4-dichlorobenzoyloxy)octadecahydro-trans-p-terphenyls and which can be expressed by the general formula

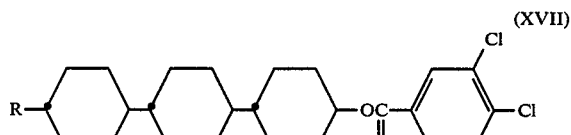

wherein R has the same definition as in claim 1.

15. Compounds as set forth in claim 1 which can be designated as 3,4-dichlorobenzoic acid-4-[trans-4-(trans-4-alkylcyclohexyl)phenyl esters and which can be expressed by the general formula

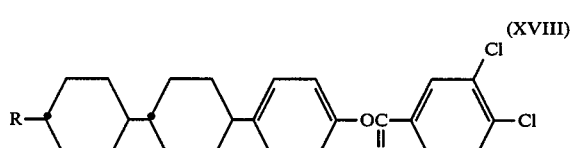

wherein R represents hydrogen atom or an alkyl group of 1 to 10 carbon atoms.

16. A liquid crystal composition comprising a mixture of compounds, at least one of which is the compound of the formula (I) of claim 1.

* * * * *